United States Patent [19]

Rasmussen

[11] 4,345,083

[45] Aug. 17, 1982

[54] (1-METHYL-2-QUINOLINYLIDENE) DERIVATIVES OF GUANIDINE

[75] Inventor: Chris R. Rasmussen, Ambler, Pa.

[73] Assignee: McNeilab, Inc., Fort Washington, Pa.

[21] Appl. No.: 102,302

[22] Filed: Dec. 10, 1979

Related U.S. Application Data

[63] Continuation of Ser. No. 943,097, Sep. 18, 1978, Pat. No. 4,266,062.

[51] Int. Cl.³ .................. C07D 401/12; A61K 31/47

[52] U.S. Cl. .................. 546/163; 424/246; 424/248.55; 424/248.56; 424/248.57; 424/250; 424/258; 424/248.52; 424/263; 544/58.6; 544/60; 544/62; 544/124; 544/128; 544/360; 544/363; 546/193; 546/194; 546/270; 546/281; 546/306; 424/248.58

[58] Field of Search .............. 546/163; 544/62, 128, 544/363

[56] References Cited

U.S. PATENT DOCUMENTS

| | | | |
|---|---|---|---|
| 2,940,974 | 6/1960 | Surry | 544/363 |
| 3,903,084 | 9/1975 | DuCharme et al. | 544/360 |
| 3,992,391 | 11/1976 | Uno | 544/360 |
| 4,021,562 | 5/1977 | Lawson et al. | 544/360 |

*Primary Examiner*—Mary C. Lee
*Assistant Examiner*—James H. Turnipseed

[57] ABSTRACT

(1-Methyl-2-pyridinylidene) and (1-methyl-2-quinolinylidene) derivatives of guanidine having hypoglycemic activity.

2 Claims, No Drawings

(1-METHYL-2-QUINOLINYLIDENE) DERIVATIVES OF GUANIDINE

This is a continuation, of application Ser. No. 943,097, filed Sept. 18, 1978 now U.S. Pat. No. 4,266,062.

BACKGROUND OF THE INVENTION

In British Pat. No. 1,409,768 there are described several heterocyclic derivatives of guanidine in which the heterocyclic moiety is a 5- or 6-membered saturated 1,3-diazacarbocyclic-2-ylidene. These derivatives are unsubstituted on the imino nitrogen of the guanidine moiety. In contrast, the compounds of the present invention differ by being a heterocyclic derivative of guanidine which carries a bulky substituent on the imino nitrogen of the guanidine moiety. Additional prior art, but further related, may be represented by German Offen. Nos. 2,321,330 and 2,502,397; U.S. Pat. Nos. 3,914,306, 3,933,836 and 4,073,636; and British Pat. No. 1,341,245.

DESCRIPTION OF THE PREFERRED EMBODIMENTS

This invention relates to new heterocyclic derivatives of guanidine having interesting pharmacological properties and, more particularly, to such derivatives having the formula:

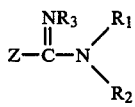

wherein:

Z is a member selected from the group consisting of:

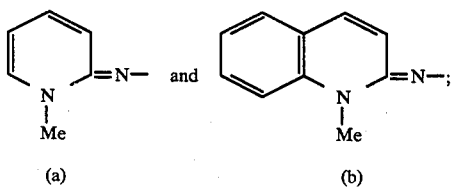

$R_1$ is a member selected from the group consisting of methyl and ethyl;

$R_2$ is a member selected from the group consisting of loweralkyl (preferably methyl and ethyl), cycloalkyl having from 3 to 6 carbons (preferably cyclopentyl and cyclohexyl) and aralkyl (preferably benzyl);

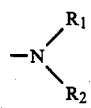

taken together represents a member selected from the group consisting of:

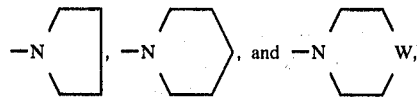

wherein W is a member selected from the group consisting of O, S, N-loweralkyl (preferably N-methyl) and N-aryl (preferably N-phenyl); and $R_3$ is a member selected from the group consisting of:
alkyl having from 4 to 10 carbons (preferably branched), such as, for example, tert-butyl, neopentyl, 1,1,- 3,3-tetramethylbutyl (tert-octyl) and the like;

phenyl; methylenedioxyphenyl; phenyl substituted with from 1 to 3 substituents each selected from the group consisting of halo, loweralkyl and loweralkoxy; and phenyl substituted with a member selected from the group consisting of hydroxy, benzyloxy, lower-alkanoyloxy, nitro; trifluoromethyl and methylthio; naphthyl;

cycloalkyl having from 5 to 8 carbons (preferably cyclopentyl and cyclohexyl);

arylalkyl in which the aryl function is a member selected from the group consisting of phenyl and naphthyl and the alkyl function has from 1 to 4 carbons, such as, for example, benzyl, dl-, d- or l-α-phenethyl, di-, d- or l-α-methylbenzyl, α,α-dimethylbenzyl, α,α-dimethyl-β-phenethyl, dl-, d- or l-(α-naphthyl)ethyl and the like; and diphenylalkyl in which the alkyl function has from 1 to 2 carbons, such as, for example, diphenylmethyl, 1,2- and 2,2-diphenylethyl and the like.

As used herein, the prefix "lower" indicates that the relevant group has 1 to 4 carbons and the term "halo" represents halogens of atomic weight less than 127, i.e., chloro, bromo, fluoro, and iodo.

Due to the presence of amine-like nitrogen atoms in the compounds of formula (I), acid addition salts thereof are readily obtained and such pharmaceutically acceptable salts are included within the scope of this invention. The subject compounds (I) may be converted to their therapeutically active nontoxic acid addition salt forms by treatment with an appropriate acid, such as, for example, an inorganic acid, such as hydrohalic acid, e.g., hydrochloric, hydrobromic and the like, and sulfuric acid, nitric acid, phosphoric acid and the like, or an organic acid, such as, for example, acetic, propionic, glycolic, pamoic, pyruvic, malonic, succinic, maleic, fumaric, malic, tartaric, citric, benzoic, cinnamic, mandelic, methane-sulfonic, ethanesulfonic, benzenesulfonic, p-toluenesulfonic, cyclohexanesulfamic, salicylic, p-aminosalicylic and the like acids. Conversely, the salt form can be converted by treatment with alkali into the free base form.

The compounds of formula (I), wherein Z, $R_1$, $R_2$, $NR_1R_2$ and $R_3$ (other than hydroxyphenyl and loweralkanoyloxyphenyl) are as previously defined, are prepared by reacting a lactam salt of formula (II), wherein X is either methoxy or ethoxy, with a guanidine derivative of formula (III), with stoichiometric quantities of reactants being preferably employed. The preparation of said guanidine derivatives (III) is described in my copending application Ser. No. 828,561, filed Aug. 29, 1977, and entitled, "Heterocyclic Derivatives of Guanidine". It is often advantageous to add four to eight molar equivalents of potassium carbonate to the reaction mixture following addition of the guanidine (III) in order to cause the reaction to proceed toward completion. Suitable anhydrous organic solvents for conducting the reaction include lower alkanols, such as, for example, 2-propanol, tert-butanol and the like; ethers, such as, for example, tetrahydrofuran, dioxane and the like; and lower halogenated hydrocarbons, such as, for example, chloroform, methylene chloride, 1,2-dichloroethane and the like. Generally, tert-butanol is prepared. Ambient to reflux temperatures (about 80° C.) may generally be employed. The product (IV), in the form of the corresponding HBF$_4$ salt, is converted to the corresponding base form (I) by conventional means, for example, by treatment with a suitable alkali such as alkali metal or alkaline earth metal hydroxides; carbonates and the like. The reaction may be illustrated as follows with Z equal to ring function (a):

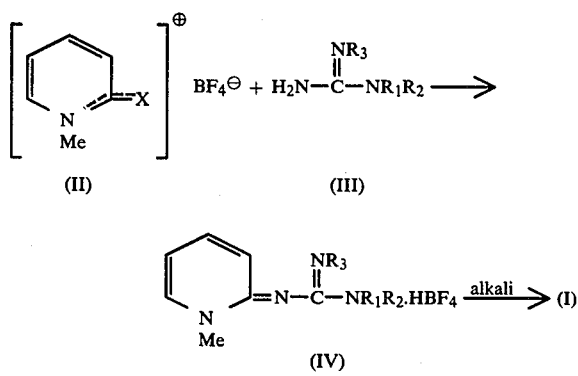

The fluoborates of formula (II) may be obtained according to procedures described in the literature, e.g., see Canadian Pat. Nos. 850,116 and 950,464; U.S. Pat. No. 3,876,658; Ber. 89, 2063 (1956); and Org. Synth. 46, 113, 120 (1966). In general, a lactam of formula (V) is reacted with an appropriate trialkyl oxonium fluoborate (VI) to give the corresponding salt (VII). The reaction is preferably carried out from 0° C. to ambient temperature under an inert dry atmosphere (e.g., nitrogen, argon) in an inert anhydrous lower halohydrocarbon solvent such as, for example, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like. The foregoing reactions may be illustrated as follows:

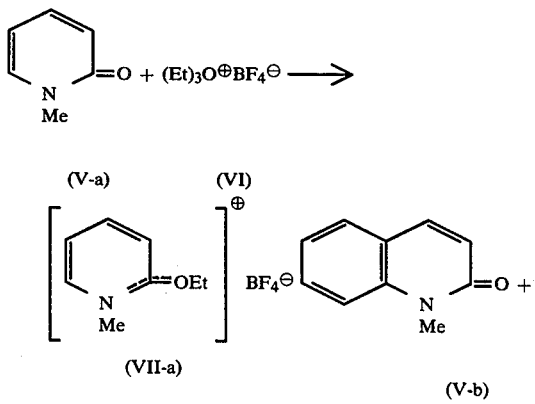

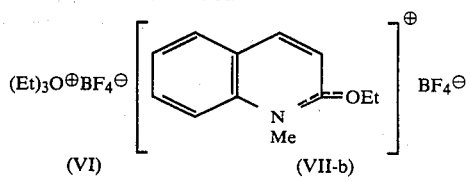

In the foregoing synthetic procedures for preparing formula (I) compounds, hydroxyphenyl and loweralkanoyloxyphenyl were excluded from the original definition of R$_3$. The formula (I) compounds wherein R$_3$ is hydroxyphenyl may be prepared by hydrolysis of either the corresponding R$_3$=methoxyphenyl or benzyloxyphenyl derivatives by conventional procedures, e.g., by treatment with HBr or HI in acetic acid. Acylation of the resultant R$_3$=hydroxyphenyl derivatives by lower alkanoic acids in the presence of excess dicyclohexylcarbodiimide affords the corresponding R$_3$=loweralkanoyloxy derivatives of formula (I).

The subject compounds of formula (I) and the acid addition salts thereof possess valuable pharmacological properties, particularly as hypoglycemic agents. Their ability to lower blood sugar is demonstrated in the following rat glucose tolerance test, which test is a standard and extremely sensitive procedure used in the diagnosis of diabetes and hypoglycemic disease states.

In this test, male Sprague-Dawley rats (Charles River 184–250 grams) are given water ad libitum and fasted 24 hours prior to the experiment. Two to five rats are used for each test and control group. Test compounds, 1–200 mg./kg., are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of Ba(OH)$_2$ and ZnSO$_4$ and glucose levels are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point are expressed in terms of milligram percent (mg glucose/100 ml of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

In addition to their hypoglycemic activity, certain of the subject compounds have been found to possess antisecretory activity and/or cardiovascular activity as demonstrated in tests described in my copending patent application Serial No. 828,561, filed Aug. 29, 1977, and entitled "Heterocyclic Derivatives of Guanidine".

The subject compounds (I), in base or salt form, may be formulated into conventional liquid and solid pharmaceutical dosage forms and preparations, for example, for oral or parenteral administration, according to standard pharmaceutical techniques in the art.

The following examples are intended to illustrate, but not to limit, the scope of the present invention. Unless otherwise stated, all parts are by weight.

EXAMPLE I

N-(1,2-Dihydro-1-methyl-2(1H)pyridinylidene)-N'-phenyl-1-pyrrolidinecarboximidamide fumarate A. Triethyloxonium fluoroborate is prepared from 3.70 g (0.040 mole) of epichlorohydrin in 14 ml of ether and 7.58 g (0.054 mole) of boron trifluoride etherate in 6 ml of ether. The resulting solid triethyloxonium tetrafluoroborate is dissolved in 20 ml of dry methylene chloride and treated under nitrogen with 4.36 g (0.040 mole) of 1-methyl-2-pyridone in 15 ml of methylene chloride. The reaction mixture is stirred under nitrogen at room temperature overnight (about 16 hours). The solvent is evaporated at room temperature, in vacuo and the quaternary salt obtained is recrystallized from methanol-ether (1:1) to give 8.0 g (71%) of 2-ethoxy-1-methylpyridinium fluoroborate, m.p. 58°–60° C.

B. A mixture of 8.00 g (0.035 mole) of the above pyridinium salt and N-phenyl-1-pyrrolidinecarboximidamide free base (obtained from 11.10 g (0.035 mole) of the corresponding hydroiodide with 3 N-sodium hydroxide, extracted in methylene chloride, dried over $K_2CO_3$, and the solvent evaporated in vacuo, at room temperature) in 50 ml of t-butanol is refluxed overnight. The reaction mixture is cooled, ether added, and the solid formed is filtered to give 10.3 g (80%) of N-(1,2-dihydro-1-methyl-2(1H)-pyridinylidene)-N'-phenyl-1-pyrrolidinecarboximidamide $HBF_4$, m.p. 184°–187° C. Recrystallization from methanol-ether gives the pure compound (by thin layer chromatography). The $HBF_4$ salt is partitioned between 3 N sodium hydroxide/methylene chloride. The organic layer is dried over potassium carbonate, filtered and evaporated in vacuo to give the base, N-(1,2-dihydro-1-methyl-2(1H)pyridinylidene)-N'-phenyl-1-pyrrolidinecarboximidamide, m.p. 145°–146.5° C.

Conversion of the free base to the fumarate salt is accomplished with an equivalent of fumaric acid in 2-propanol. Recrystallization from 2-propanol-ether (some methanol is added to the 2-propanol suspension to dissolve the same and then boiled off) gives 9.6 g of N-(1,2-dihydro-1-methyl-2(1H)pyridinylidene)-N'-phenyl-1-pyrrolidinecarboximidamide fumarate, m.p. 183°–185.5° C.

EXAMPLE II

By reacting an equivalent amount of an appropriate guanidine of formula (III) with the pyridinium salt, 2-ethoxy-1-methylpyridinium fluoroborate, according to the procedure of Example I, the following respective products of formula (I) are obtained, as the free base or by conversion to the indicated acid addition (HX) salt:

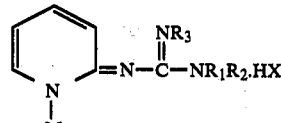

| No. | R₃ | —NR₁R₂ | HX |
|---|---|---|---|
| 1 | 4-F—2-Me—Ph | —N(Me)(2-thienyl) | fumarate |
| 2 | 3-Br—Ph | -N(pyrrolidinyl) | HCl |
| 3 | 2,3,4-triCl—Ph | -N(piperidinyl) | maleate |
| 4 | 4-Br—2-Cl—Ph | —NEt₂ | HO₃SMe |
| 5 | 4-OEt—Ph | -N(piperazinyl-NPh) | base |
| 6 | 3,4,5-triOMe—Ph | -N(piperidinyl) | HI |
| 7 | 2-Et—6-Me—Ph | —NEt₂ | fumarate |
| 8 | 4-n-Bu—Ph | -N(morpholinyl) | base |
| 9 | diphenylmethyl | -N(piperidinyl) | HCl |
| 10 | α,α-diMe—phenethyl | —NMe₂ | base |
| 11 | 1-adamantyl | —NEt₂ | succinnate |
| 12 | endo-2-norbornyl | -N(morpholinyl) | fumarate |
| 13 | tert-octyl | -N(pyrrolidinyl) | base |
| 14 | Ph | -N(morpholinyl) | fumarate |
| 15 | 4-OBz—Ph | —NEt₂ | base |
| 16 | exo-2-norbornyl | -N(pyrrolidinyl) | HCl |
| 17 | 4-SMe—Ph | -N(morpholinyl) | benzoate |
| 18 | cyclopentyl | —NE₂ | HBr |

-continued

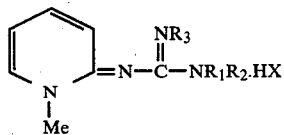

| No. | R₃ | —NR₁R₂ | HX |
| --- | --- | --- | --- |
| 19 | 1-naphthyl | N(Me)—⟨S⟩ (thiazolidine) | HBr |
| 20 | 2,2-diphenethyl | —N⟨ ⟩S (thiomorpholine) | base |
| 21 | Bz | —NEt₂ | HCl |
| 22 | 4-OMe—Ph | —NEt₂ | HCl |

EXAMPLE III

N-(1,2-Dihydro-1-methyl-2(1H)-quinolinylidene-N'-phenyl-1-pyrrolidinecarboximidamide fumarate (1:1.5)

A. Triethyloxonium fluoroborate is prepared from 3.70 g (0.040 mole) of epichlorohydrin in 14 ml of ether and 7.58 g (0.054 mole) of boron trifluoride etherate in 6 ml of ether. The resulting solid triethyloxonium fluoroborate is dissolved in 20 ml of dry methylene chloride and treated under nitrogen with 6.47 g (0.040 mole) of N-methyl-2-quinolone in 15 ml of methylene chloride. The reaction mixture is stirred under nitrogen at room temperature overnight. The solid is filtered to give 9.2 g (83.5%) of 2-ethoxy-1-methylquinolinium fluoroborate.

B. A mixture of 8.50 g (0.031 mole) of the above quinolinium salt and N-phenyl-1-pyrrolidinecarboximidamide in 150 ml of t-butanol is refluxed for 24 hours. The reaction mixture is evaporated in vacuo and the gummy residue covered with methanol and chilled. The resulting solid is filtered to give 11.2 g (86.8%) of N-(1,2-dihydro-1-methyl-2(1H)-quinolinylidene-N'-phenyl-1-pyrrolidinecarboximidamide HBF₄, m.p. 161.5°–164° C. Recrystallization from methanol-ether yields the pure HBF₄ salt (by TLC), 9.0 g, m.p. 166°–169° C. The HBF₄ salt is partitioned between 3 N-sodium hydroxide and methylene chloride. The organic layer is dried over potassium carbonate, filtered, and evaporated in vacuo to give the N-(1,2-dihydro-1-methyl-2(1H)-quinolinylidene-N'-phenyl-1-pyrrolidenecarboximidamide as a yellow solid, 6.7 g (80.6%). Conversion of the free base to the fumarate is accomplished with one equivalent of fumaric acid (2.9 g, 0.025 mole) in 2-propanol. Two recrystallizations from 2-propanol-ether give 7.5 g of pure N-(1,2-dihydro-1-methyl-2(1H)-quinolinylidene)-N'-phenyl-1-pyrrolidinecarboximidamide fumarate (1:1.5), m.p. 209°–211° C. (dec.).

EXAMPLE IV

By following the procedure of Example III, except that an equivalent amount of an appropriate guanidine of formula (III) is reacted with the quinolinium salt, 2-ethoxy-1-methylquinolinium fluoroborate, the following respective products of formula (I) are obtained, as the free base or by conversion to the indicated acid addition (HX) salt:

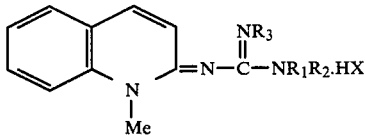

| No. | R₃ | —NR₁R₂ | HX |
| --- | --- | --- | --- |
| 1 | 3-CF₃—Ph | —N⟨ ⟩O (morpholino) | HO₃S—⟨Ph⟩—Me |
| 2 | 3,4-diCl—Ph | —N(Me)—⟨S⟩ | HBr |
| 3 | 5-Cl—2,4-diOMe—Ph | —N⟨ ⟩N—Ph (piperazinyl) | HCl |
| 4 | 4-I—Ph | —N⟨ ⟩O (morpholino) | base |
| 5 | 4-OMe—2-Me—Ph | —N(Me)Bz | base |
| 6 | 4-OBz—Ph | —N⟨ ⟩ (piperidino) | fumarate |

-continued

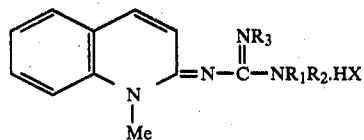

| No. | R₃ | —NR₁R₂ | HX |
|---|---|---|---|
| 7 | 2,4,5-triMe—Ph | -N(pyrrolidinyl) | succinate |
| 8 | 4-NO₂—Ph | -N(thiomorpholinyl) | HCl |
| 9 | d,1-α-Me—Bz | -N(N'-Me-piperazinyl) | base |
| 10 | 1,2-diphenethyl | -N(pyrrolidinyl) | HI |
| 11 | cyclohexyl | —N(Me)—(thienyl) | fumarate |
| 12 | tert-butyl | -N(thiomorpholinyl) | HCl |
| 13 | 3,4-methylenedioxy-Ph | —N(Me)Bz | fumarate |
| 14 | 4-OBz—Ph | -N(N'-Ph-piperazinyl) | 2 HI |
| 15 | Ph | —NEt₂ | HCl |
| 16 | 1-adamantyl | —NEt₂ | HCl |
| 17 | d,1α-Me—B | —NMe₂ | HBr |
| 18 | exo-2-norbornyl | -N(piperidinyl) | base |
| 19 | benzhydryl | -N(pyrrolidinyl) | base |
| 20 | Bz | —N(IsoPr)₂ | H₂SO₄ |
| 21 | neopentyl | -N(pyrrolidinyl) | HCl |
| 22 | 4-OMe—Ph | —NEt₂ | HCl |

EXAMPLE V

N'-(4-Methoxyphenyl)-N-(1,2-dihydro-1-methyl-2(1H)-pyridinylidene)-1-piperidinecarboximidamide hydroiodide A 100 ml round-bottomed flask is charged with 0.0126 mole of N-(4-methoxyphenyl)-1-piperidinecarboximidamide, 5.2 g (0.037 mole) of anhydrous potassium carbonate, 3.39 g (0.014 mole) of 2-ethoxy-1-methylpyridinium fluoborate and 20 ml of t-BuOH. The mixture is allowed to reflux overnight. After filtration, the solvent is removed in vacuo, and the residue taken up in methylene chloride and shaken with cold 20% NaOH. The organic layer is dried (K₂CO₃), filtered and the solvent removed in vacuo. Conversion to the HI salt in ether solution, affords N'-(4-methoxyphenyl)-N-(1,2-dihydro-1-methyl-2(1H)-pyridinylidene)-1-piperidinecarboximidamide hydroiodide.

EXAMPLE VI

N'-(4-Hydroxyphenyl-N-(1,2-dihydro-1-methyl-2(1H)-pyridinylidene)-1-piperidinecarboximidamide monohydroiodide A 50 ml round-bottomed flask is charged with 0.00690 mole of N'-(4-methoxyphenyl)-N-(1,2-dihydro-1-methyl-2(1H)-pyridinylidene)-1-piperidinecarboximidamide hydroiodide, 5.89 g (0.021 mole) of 50% HI and 6.0 g of glacial acetic acid. This mixture is heated under reflux for 6 hr. Evaporation of the solvent and excess HI in vacuo gives N'-(4-hydroxyphenyl-N-(1,2-dihydro-1-methyl-2(1H)-pyridinylidene)-1-piperidinecarboximidamide monohydroiodide.

EXAMPLE VII

N-(4-methoxyphenyl)-N'-(1,2-dihydro-1-methyl-2(1H)-quinolinylidene)-1-piperidinecarboximidamide A mixture of 0.010 mole of N-(4-methoxyphenyl)-1-piperidinecarboximidamide, 2.89 g (0.011 mole) of 2-ethoxy-1-methylquinolinium tetrafluoroborate, 4.14 g (0.030 mole) of $K_2CO_3$ and 20 ml of t-BuOH is allowed to reflux overnight protected by a $CaCl_2$ drying tube. The reaction mixture is filtered and the solvents evaporated in vacuo. The residue is treated with cold 20% NaOH and extracted with $CH_2Cl_2$. The combined organic layers are dried ($K_2CO_3$), filtered and evaporated in vacuo to give N'-4-methoxyphenyl)-N-(1,2-dihydro-1-methyl-2(1H)-quinolinylidene)-1-piperidinecarboximidamide in the free base form.

EXAMPLE VIII

N-(4-hydroxyphenyl)-N'-(1,2-dihydro-1-methyl-2(1H)-quinolinylidene-1-piperidinecarboximidamide hydroiodide A mixture of 0.01 mole of N-(4-methoxy-N'-(1,2-dihydro-1-methyl-2(1H)-quinolinylidene-1-piperidinecarboximidamide, 7.57 g (0.03 mole) of 50% HI, and 7.0 g of glacial acetic acid is heated under reflux for 6 hr. Solvent and excess HI are removed in vacuo to give N-(4-hydroxyphenyl)-N'-(1,2-dihydro-1-methyl-2(1H)-quinolinylidene-1-piperidinecarboximidamide hydroiodide.

EXAMPLE IX

N-(4-Acetoxyphenyl)-N'-(1,2-dihydro-1-methyl-2(1H)-quinolinylidene-1-piperidinecarboximidamide hydroiodide A solution of 0.01 mole of the compound of Example VIII in 10 ml of glacial HOAc and 20 ml of methylene chloride is treated with 20.6 g (0.1 mole) of dicyclohexylcarbodiimide under argon. After stirring at ambient temperatures overnight, the formed dicyclohexylurea is removed by filtration and the filtrate is taken to dryness in vacuo. The residue is triturated with anhydrous ether (3 × 100 ml) to remove unchanged dicyclohexylcarbodiimide, leaving as the residue, N-(4-acetoxyphenyl)-N'-(1,2-dihydro-1-methyl-2(1H)-quinolinylidene-1-piperidinecarboximidamide hydroiodide.

EXAMPLE X

N-(4-Acetoxyphenyl)-N'-(1,2-dihydro-1-methyl-2(1H)-pyridinylidene-1-piperidinecarboximidamide hydroiodide A solution of 0.01 mole of the compound of Example VI in 10 ml of glacial acetic acid and 20 ml of methylene chloride is treated with 20.6 g (0.1 mole) of dicyclohexylcarbodiimide under argon and the solution is allowed to stir overnight. Workup according to the procedure of Example VI affords as the residue, N-(4-acetoxyphenyl)-N'-(1,2-dihydro-1-methyl-2(1H)-piperidinylidene-1-piperidinecarboximidamide hydroiodide.

What is claimed is:

1. A heterocyclic derivative of guanidine selected from the group consisting of a compound having the formula:

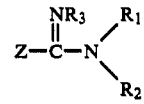

and the pharmaceutically-acceptable acid addition salts thereof wherein:

Z is

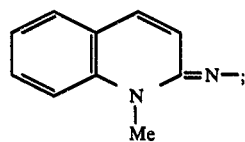

$R_1$ is a member selected from the group consisting of methyl and ethyl;

$R_2$ is a member selected from the group consisting of loweralkyl, cyclopentyl, cyclohexyl and benzyl;

taken together represents a member selected from the group consisting of:

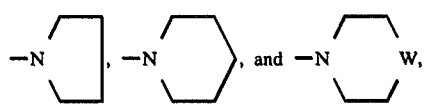

wherein W is a member selected from the group consisting of O, S, N-loweralkyl and N-phenyl; and $R_3$ is a member selected from the group consisting of:
alkyl having from 4 to 10 carbons;
phenyl; methylenedioxyphenyl; phenyl substituted with
from 1 to 3 substituents each selected from the group consisting of halo, loweralkyl and loweralkoxy; and phenyl substituted with a member selected from the group consisting of hydroxy, benzyloxy, loweralkanoyloxy, nitro; trifluoromethyl and methylthio;
naphthyl; cyclopentyl; cyclohexyl; exo-2-norbornyl; endo-2-norbornyl; 1-adamantyl;
arylalkyl in which the aryl function is phenyl and the alkyl function has from 1 to 4 carbons; and diphenyl in which the alkyl function has from 1 to 2 carbons.

2. A compound selected from the group consisting of N-(1,2-dihydro-1-methyl-2(1H)quinolinylidene)-N'-phenyl-1-pyrrolidinecarboximidamide and the pharmaceutically acceptable acid addition salts thereof.

* * * * *